US007360392B2

(12) United States Patent
Konzelmann et al.

(10) Patent No.: US 7,360,392 B2
(45) Date of Patent: Apr. 22, 2008

(54) FLUID SENSOR INCLUDING AN ERROR DETECTION DEVICE

(75) Inventors: Uwe Konzelmann, Asperg (DE); Ulrich Wagner, Stuttgart (DE); Christoph Gmelin, Stuttgart (DE); Martin Baumann, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/715,573

(22) Filed: Mar. 7, 2007

(65) Prior Publication Data

US 2007/0289356 A1 Dec. 20, 2007

(30) Foreign Application Priority Data

Mar. 9, 2006 (DE) ..................... 10 2006 010 901

(51) Int. Cl.
*G01B 27/04* (2006.01)

(52) U.S. Cl. ...................................................... 73/1.02

(58) Field of Classification Search ................ 73/1.02, 73/1.06

See application file for complete search history.

(56) References Cited

U.S. PATENT DOCUMENTS 5,212,989 A * 5/1993 Kodama et al. .............. 73/706
6,644,113 B2 * 11/2003 Kawai et al. ............ 73/204.26
6,777,961 B2 * 8/2004 Hamamoto et al. ......... 324/703
6,953,630 B2 * 10/2005 Wells .......................... 429/13
2004/0232911 A1 * 11/2004 Schlicker et al. ........... 324/242
2007/0107527 A1 * 5/2007 Ogisu et al. .................. 73/774
2007/0181111 A1 * 8/2007 Cullen ........................ 123/677

OTHER PUBLICATIONS

Michael Amdt, "Micromachined Thermal Conductivity Hydrogen Detector for Automotive Applications", 5 pages, 2002, Sensors, IEEE Proceedings.

* cited by examiner

*Primary Examiner*—Hezron Williams
*Assistant Examiner*—John Fitzgerald
(74) *Attorney, Agent, or Firm*—Kenyon & Kenyon LLP

(57) ABSTRACT

A fluid sensor may be used for detecting fluid media, in particular hydrogen. The fluid sensor includes a sensor chip having a chip surface, which has a measuring surface and a body surface. Printed conductors of a central sensor circuit having at least one heating element and at least one temperature sensor are provided on the measuring surface. Furthermore, the fluid sensor has one additional fracture detection element and one fracture detection circuit situated on the sensor chip. The fracture detection circuit is designed for detecting fractures and/or cracks in and/or on the sensor chip, in particular in the area of a boundary between the measuring surface and body surface.

16 Claims, 3 Drawing Sheets

FLUID SENSOR INCLUDING AN ERROR DETECTION DEVICE

FIELD OF THE INVENTION

The present invention relates to a fluid sensor for detecting fluid media, in particular gases such as hydrogen, for example. Sensors of this type are used, for example, in automotive engineering for detecting and/or measuring the concentration of hydrogen in a hydrogen-air mixture.

BACKGROUND INFORMATION

In many processes, for example, in the area of process engineering, chemistry or mechanical engineering, gas concentrations must be reliably determined and/or a defined quantity of a gas mass, in particular an air mass, must be supplied. These include in particular combustion processes, which must proceed under controlled conditions. An important example is the combustion of fuel in internal combustion engines of motor vehicles, in particular those having subsequent catalytic exhaust gas purification. Another area of application is the supply of gases of a highly specific composition for fuel cells. Safety-relevant applications are also of significance. For example, a hydrogen sensor may be used in fuel cell vehicles in order to warn passengers of a slow escape of hydrogen. Air becomes ignitable at a hydrogen concentration of roughly 4% and even becomes explosive at higher concentrations so that the hydrogen sensor may be linked, for example, to an appropriate warning device or an appropriate automatic emergency system. Other safety-relevant applications of gas sensors of this type are also conceivable.

Various types of sensors are used for measuring a gas stream and/or a gas concentration. One category of such sensors includes sensors having a sensor chip. A type of sensor of this category known from the related art is the hot film air mass sensor (HFM), an embodiment of which is described, for example, in German Patent Application No. DE 196 01 791. Normally used in such hot film air mass sensors is a sensor chip having a thin sensor diaphragm, for example a silicon sensor chip. Typically, at least one heating resistor is situated on the sensor diaphragm, the heating resistor being surrounded by one or more temperature measuring resistors (temperature sensors). The temperature distribution in an air stream passing across the diaphragm changes, which may in turn be detected by the temperature measuring resistors and analyzed using an actuation and analysis circuit. It is thus possible, for example, to determine an air mass flow from a resistance difference of the temperature measuring resistors. Various other versions of this sensor type are known from the related art.

In addition to the detection of a flow, the detection and measurement of components making up the particular gaseous fluid is also of great significance. A sensing principle is based on the varying thermal capacity and/or thermal conductivity of the different fluid components and is described, for example, in M. Arndt: "Micromachined Thermal Conductivity Hydrogen Detector for Automotive Applications," Sensors, 2002. Proceedings of IEEE. For example, the detection of hydrogen in an air-hydrogen mixture makes use of the fact that hydrogen has a higher thermal conductivity than air, i.e., the components of air. In a sensor configuration designed similar to hot film air mass sensors (HFM), an air-hydrogen mixture diffuses through a thin diaphragm or a tight mesh into a measuring space of a sensor. The presence of hydrogen in the gaseous fluid changes the temperature of the heated measuring diaphragm or its thermal output which is given off to the ambient air. A measuring signal is generated from this which reflects the concentration of the hydrogen.

As described above, typical chip gas sensors are designed in such a way that they have a sensor diaphragm (for example, a silicon diaphragm) having low thermal conductivity and a surrounding chip body. Electrically conductive structures are situated on this sensor diaphragm. However, the chip frequently cracks and/or fractures when such sensors are put into practical use, in particular in the area of the transition between the sensor diaphragm and the chip body, usually due to the presence there of thermal and/or mechanical stresses related to design or operation. Experience shows that these fractures or cracks mostly extend in or along the edges of the sensor diaphragm at the transition to the chip body. Such fractures may result in complete or partial failure of the sensor and/or the output of corrupted signals. As long as these cracks or fractures do not affect any printed conductors of the sensor, the sensor will usually continue to generate electrical signals; however, they are corrupted due, for example, to the changed thermal conductivity of the sensor diaphragm and/or the changed thermal connection of the diaphragm to the chip body. Because the sensor is used in safety-relevant applications in many cases, for example, in fuel cells, such erroneous indications are usually not tolerable.

SUMMARY OF THE INVENTION

The present invention describes a fluid sensor for detecting fluid media which reliably and dependably detects the above-described fractures and/or cracks, thus making reliable error detection possible. The present invention is based on the idea of implementing the printed conductors required for the measurement functions on the diaphragm of fluid sensors. These printed conductors cross the diaphragm or the transition between the diaphragm and body at a few places. If a crack forms in the vicinity of the boundary and the chip body which does not break through these printed conductors and thus does not result in a total failure of the sensor, the detection of such a crack or fracture is very complex in the methods known heretofore. In such case, the detection is only possible, for example, by performing an optical inspection or plausibility checks against additional signal sources and/or using a measurement history As in the related art, the fluid sensor of the present invention has a sensor chip including a chip surface which may be exposed to the fluid medium. This chip surface contains a measuring surface and a body surface. As described above, this may be a silicon chip, for example. In the area of the measuring surface, the sensor chip may, for example, be designed in such a way that it has a transversal thermal conductivity which is lower by at least one order of magnitude than in the area of the body surface. As in the hot film air mass sensor chip described above, this may, for example, be achieved by using sensor chips having a thin sensor diaphragm of a thickness of only a few micrometers. This makes use of the low thermal conductivity (approximately 0.026 W/mK) of the air (or an alternative gas) surrounding the sensor diaphragm. Alternatively, porous areas may be produced in the chip as a measuring area having a measuring surface facing the fluid medium to be measured, for example by porosifying a silicon chip. In this way, it is possible to produce measuring areas that, due to the enclosed air cavities, have a transversal conductivity of 0.1 to 2 W/mK compared to a silicon substrate having a thermal conductivity of approximately 156 W/mK. Printed conductors of a central sensor circuit having at least one heating element and at least one temperature sensor are provided on the measuring surface (or in the vicinity of this measuring surface). Furthermore, according to the present invention, the fluid sensor has at least one additional fracture detection element and one fracture detection circuit situated on the sensor chip. The fracture detection circuit is designed to detect fractures and/or cracks in and/or on the sensor chip, in particular in the area of the transition between the measuring surface and body surface.

The at least one fracture detection element and the at least one fracture detection circuit cooperate to make possible a reliable and dependable detection of fractures and/or cracks, preferably independent of the other functionality of the fluid sensor. For example, the at least one fracture detection element may include at least one fracture detector printed conductor. This at least one fracture detector printed conductor may extend, for example, in at least one area, in a serpentine or meander pattern in the area of the transition between the measuring surface and body surface. It is preferred for this at least one fracture detector printed conductor to cross the boundary between the measuring surface and the body surface a plurality of times in this at least one area. In this way, the boundary between the measuring surface and the body surface, which is in particular susceptible to fractures and/or cracks, is covered in a particularly efficient manner and errors in this area are efficiently detected.

Alternatively or additionally, the at least one fracture detector printed conductor may include at least one first printed conductor segment extending on the measuring surface at least approximately parallel to the boundary between the measuring surface and the body and at least one second printed conductor segment extending on the body surface at least approximately parallel to the boundary between the measuring surface and the body surface. In this manner, the parallel printed conductor segments cover a strip which extends parallel to the boundary between the measuring surface and the body surface and efficiently covers this area which is particularly critical.

It is preferred in particular that the at least one fracture detection element is situated in at least one area on the measuring surface at a distance of 10 to 100 micrometers, preferably 20 to 50 micrometers, and most preferably at a distance of 25 micrometers from the boundary between the measuring surface and body surface. For example, the meander or serpentine pattern described above may extend from the boundary into this measuring surface by these 25 micrometers. Alternatively or additionally, the at least one first printed conductor segment described above may be situated on the measuring surface at this preferred distance of 25 micrometers from the boundary.

Similarly, it is also preferred that the at least one fracture detection element extends in at least one area at a distance of 10 to 100 micrometers, preferably 20 to 50 micrometers, and most preferably at a distance of 25 micrometers from the boundary between the measuring surface and body surface onto the body surface. For example, the meander and/or serpentine pattern may extend from the boundary to this body surface by these preferred 25 micrometers. Alternatively or additionally, the at least one second printed conductor segment described above may be situated on the body surface at a distance of preferably 25 micrometers from the boundary between the measuring surface and body surface.

Furthermore, the fracture detection circuit of the fluid sensor according to one of the embodiments described above may have at least one circuit for detecting a resistance. This embodiment is preferred in particular if the at least one fracture detection element includes at least one fracture detector printed conductor. For example, the fracture detection circuit may also have at least one threshold circuit designed for comparing the detected resistance with at least one threshold value and generating at least one control signal as a function of the result of the comparison. This makes it possible, for example, to detect a fracture and/or crack which influences the at least one fracture detection element, preferably the at least one fracture detector printed conductor, based on an abrupt increase of the detected resistance. Such a circuit for detecting a resistance or such a threshold circuit is technically considerably less complex and more economical than the circuits described above which, for example, perform a plausibility check of the fluid sensor signals to detect fractures.

FIG. **2*a*** shows an exemplary embodiment of a hydrogen sensor according to the present invention having a fracture detection element and a fracture detection circuit.

Figure 2A:
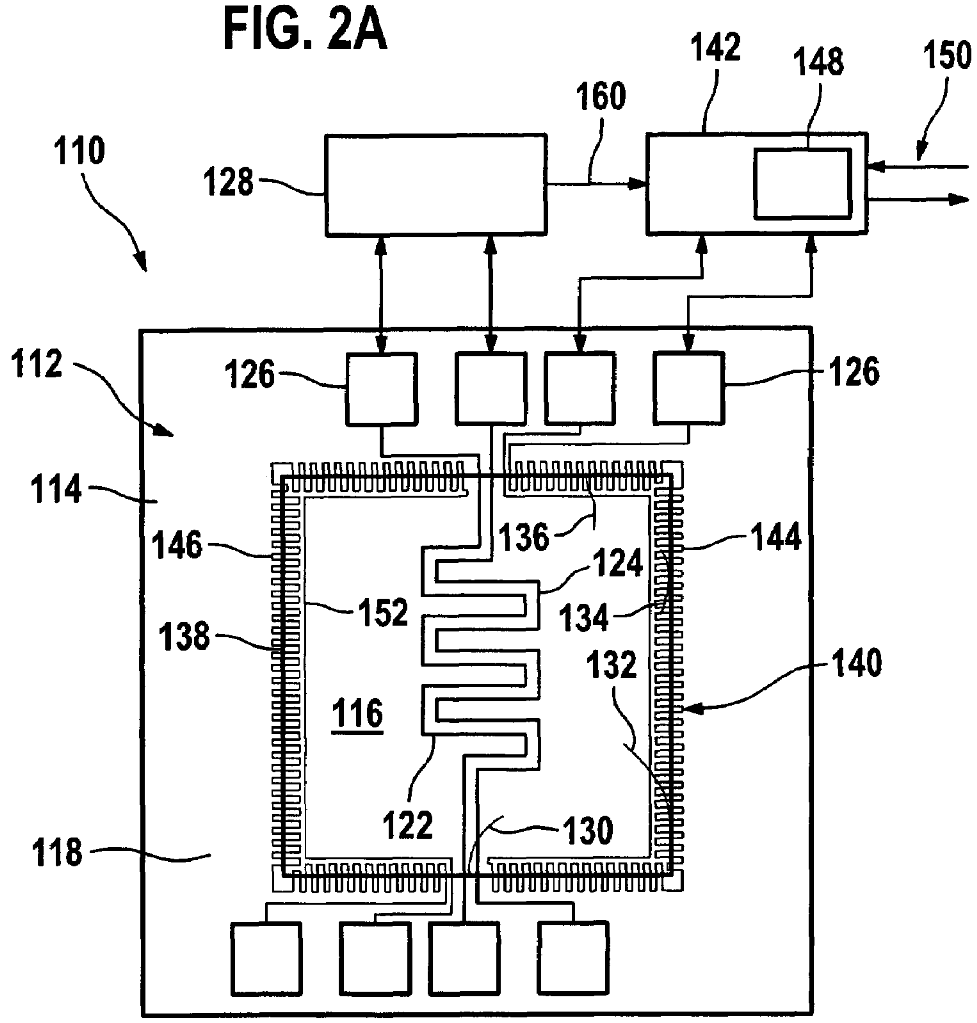

FIG. **2*b* shows a detail of the hydrogen sensor according to FIG. 2*a***.

Figure 2B:
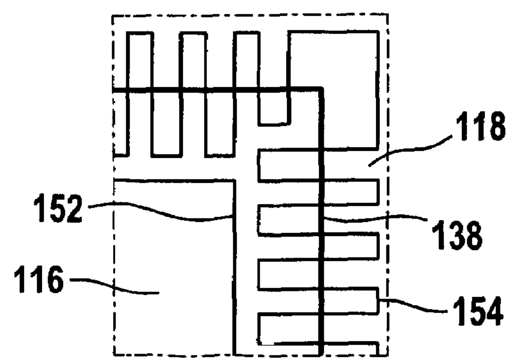
Figure 3:
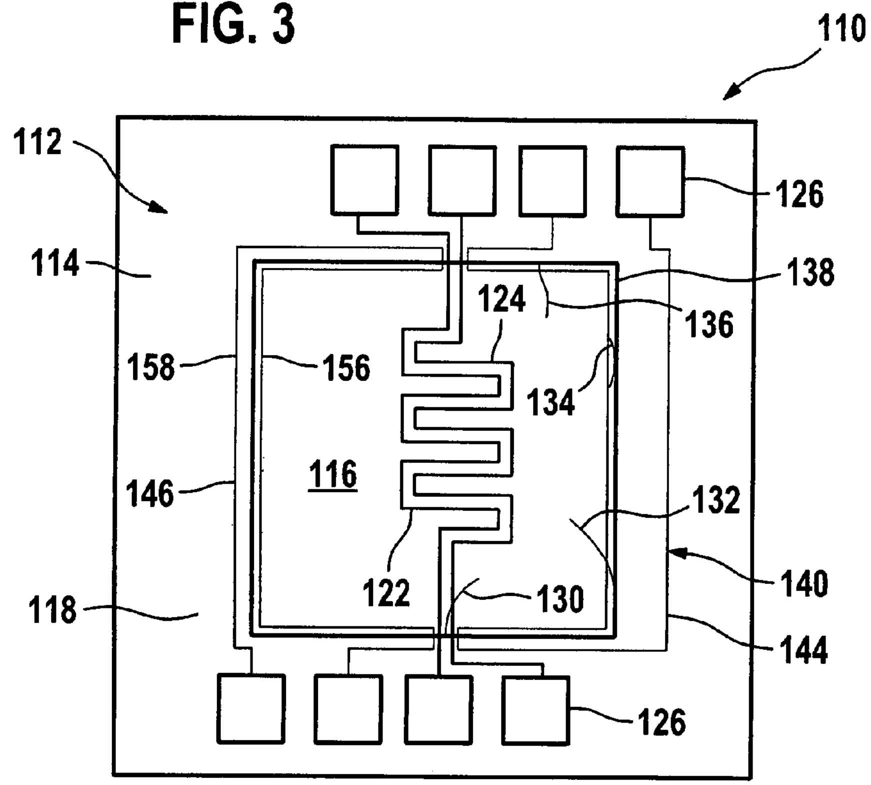

FIG. 3 shows an exemplary embodiment of a hydrogen sensor as an alternative to FIG. 2.

Figure 4:
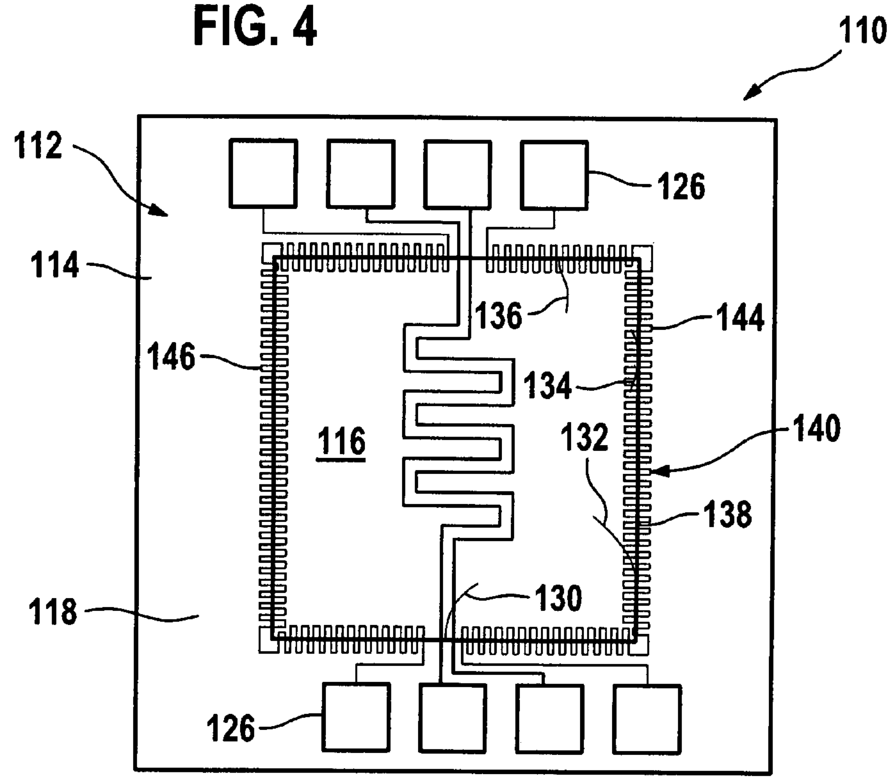

FIG. 4 shows an exemplary embodiment of a hydrogen sensor as an alternative to FIGS. 2 and 3.

DETAILED DESCRIPTION

Figure 1:
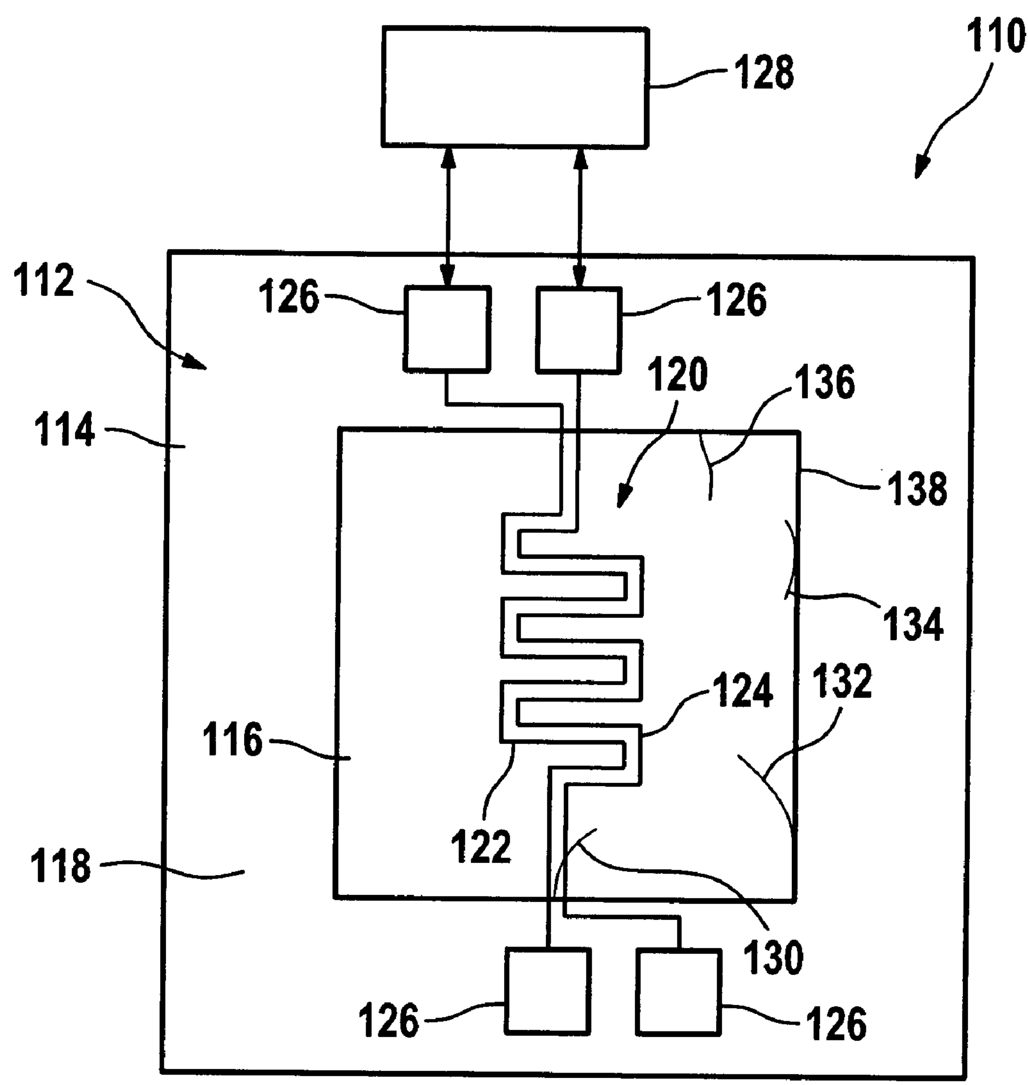
FIG. 1 shows a structure of a hydrogen sensor corresponding to the related art.

An exemplary embodiment of a fluid sensor 110 which is known from the related art is shown in FIG. 1, the fluid sensor in this case being designed as a hydrogen sensor. Such a fluid sensor 110 is known, for example, in the publication by M. Arndt described above. The fluid sensor includes a sensor chip 112 having a chip surface 114, which may be exposed to a gas mixture.

The chip surface has a measuring surface 116 and a body surface 118. In the exemplary embodiment, sensor chip 112 may be, for example, a silicon chip having a diaphragm of silicon oxide and/or silicon nitride in the area of measuring surface 116.

A central sensor circuit 120 having a heating element printed conductor 122 and a temperature sensor printed conductor 124 is provided on measuring surface 116. Contact pads 126 of printed conductors 122, 124 are connected to an actuation and analysis circuit 128 which determines a hydrogen concentration according to the principle described above.

Four variously positioned cracks 130, 132, 134, 136 are shown symbolically in FIG. 1 in order to illustrate the problems of a “diaphragm crack.” Of these variously positioned cracks 130 through 136, which normally occur in the area of boundary 138 between measuring surface 116 and body surface 118, only cracks of the type denoted as crack 130 are detected by the circuit according to the related art shown in FIG. 1. Only crack 130 directly interrupts printed conductor 122, 124 of central sensor circuit 120.

In contrast, embodiments of a fluid sensor 110 according to the present invention are shown in FIGS. **2*a* through 4, the fluid sensor 110 having fracture detection elements 140 and a fracture detection circuit 142. The system is only shown schematically in these figures, in particular the connection between terminal pads 126 and actuation and analysis circuit 128 or fracture detection circuit 142. In these exemplary embodiments of the present invention, fracture detection elements 140 have individual printed conductors 144, 146, which are isolated from printed conductors 124, 126. These individual fracture detector printed conductors 144, 146 are situated in the vicinity of boundary 138 between measuring surface 116 and body surface 118. Therefore, a high probability exists that cracks in measuring surface 116 in the vicinity of this boundary 138 will interrupt this fracture detector printed conductor 144, 146. It is easily possible to detect this interruption electrically using fracture detection circuit 142. It is correspondingly possible for fracture detection circuit 142, which includes a simple threshold circuit 148 in this exemplary embodiment, to detect if a resistance of fracture detector printed conductor 144, 146 exceeds a threshold value. If this threshold value is exceeded, an error signal may be generated and output, for example, via an interface 150. A status of fluid sensor 110** may be set to "diaphragm crack" in this manner, for example.

Fracture detection circuit 142 is only shown in the exemplary embodiment according to FIG. 2*a* and must be supplemented as appropriate in the other figures. The various embodiments relate in particular to the shape and exact position of fracture detector printed conductors 144 of fracture detection element 140. Basically, the following parameters in particular may be varied:

- dimensions of fracture detector printed conductors 144, 146 (width, length, height, number of folds of a meander, etc.),
- extension of printed conductors 144, 146 on body surface 118,
- shape of fracture detector printed conductors 144, 146 (meander shape, serpentine shape, right-angled, circular arc shaped, zig-zag, etc.),
- number of the meanders or serpentines (for more exact localization of the cracks for freer leads to the printed conductors).

FIG. 2*a* shows an embodiment preferred in particular which is able to detect all types of cracks 130 through 136. In this embodiment, fracture detection element 140 has two fracture detector printed conductors 144, 146. These fracture detector printed conductors 144, 146 thus divide fracture detection element 140 into two independent circuits, offering the advantage that it is unnecessary to cross printed conductors 122, 124 of central sensor circuit 120. These printed conductors 122, 124 may continue to be routed away from measuring surface 116 at two diametrically opposed edges as is also the case in the related art (see FIG. 1). In addition, fracture detector printed conductors 144, 146 also function as a heat sink.

In the embodiment in FIGS. 2*a* and 2*b*, fracture detector printed conductors 144, 146 have a meander shape. These fracture detector printed conductors 144, 146 each have a straight printed conductor segment 152, which in this exemplary embodiment extends at a distance of approximately 25 micrometers from boundary 138 between measuring surface 116 and body surface 118 parallel to this boundary 138. Furthermore, fracture detector printed conductors 144,146 have meander-shaped segments 154 which cross boundary 138 perpendicularly multiple times (see enlarged detail representations in FIG. 2*b*).

In the exemplary embodiment according to FIG. 2*a*, sensor chip 112 has a roughly square shape. Measuring surface 116 has an edge length of typically 1 millimeter in this exemplary embodiment. In this example, fracture detector printed conductors 144, 146 extend over an area of approximately 25 micrometers from boundary 138 into measuring surface 116 and by roughly the same amount into body surface 118. In this manner, fracture detector printed conductors 144, 146 each cover a strip-shaped area of a width of approximately 50 micrometers around boundary 138 between measuring surface 116 and body surface 118. Other dimensions of fracture detector printed conductors 144, 146 are of course also possible.

In the exemplary embodiment according to FIG. 3 as well, fracture detection element 140 has two fracture detector printed conductors 144, 146. These fracture detector printed conductors 144, 146 are again designed as printed conductor loops, each of which being contactable via terminal pads 126. Terminal pads 126 of fracture detector printed conductors 144, 146 are each located on diametrically opposed sides of measuring surface 116.

In contrast to the exemplary embodiment according to FIG. 2*a*, fracture detector printed conductors 144, 146 in the exemplary embodiment according to FIG. 3 do not have a meander shape. Instead, the printed conductor loops of fracture detector printed conductors 144, 146 each have a first printed conductor segment 156 and a second printed conductor segment 158, first printed conductor segment 156 extending on measuring surface 116 parallel to boundary 138 and second printed conductor segment 158 extending parallel to boundary 138 on body surface 118. In this exemplary embodiment, the first printed conductor segment is at a distance of approximately 25 micrometers from boundary 138, second printed conductor segment 158 being at a distance of approximately 100 micrometers. This system makes it possible to detect cracks in exemplary cracks 130, 132 and 136 shown in this manner. However, the detection of cracks running roughly parallel to boundary 138, such as crack 134, for example, is less reliable using this version.

Finally, a third exemplary embodiment of a fluid sensor 110 is shown in FIG. 4. This fluid sensor 110 again has a fracture detection element 140 having two fracture detector printed conductors 144, 146. In contrast to the exemplary embodiments in FIG. 2*a* and FIG. 3, in the exemplary embodiment according to FIG. 4 these fracture detector printed conductors 144, 146 are not designed as printed conductor loops but instead they have terminal pads 126 on diametrically opposed sides of measuring surface 116. In this manner, straight printed conductor segment 152 according to the example in FIG. 2*a* does not exist in this exemplary embodiment. This embodiment therefore makes it possible to reliably detect cracks of the type denoted as 130, 132 and 134; however, cracks of type 136 which run approximately perpendicular to boundary 138 are detected less reliably. As is also the case in the exemplary embodiment according to FIGS. 2*a*, 2*b* and 3 above, fracture detection circuit 142 advantageously uses information of actuation and analysis circuit 128 (denoted by arrow 160 in FIG. 2*a*) in addition to a resistance measurement of fracture detector printed conductors 144, 146. In this manner, of course, cracks in the area of printed conductors 122, 124 also contribute to the fracture detection.

What is claimed is:

1. A fluid sensor for detecting fluid media, comprising:

a sensor chip having a chip surface which can be exposed to the fluid medium, the chip surface having a measuring surface and a body surface, and having printed conductors of a central sensor circuit having at least one heating element and at least one temperature sensor situated on the measuring surface;

at least one fracture detection element situated on the sensor chip; and a fracture detection circuit for detecting at least one of (a) fractures and (b) cracks, in and/or on the sensor chip.

2. The fluid sensor according to claim 1, wherein the fluid media include gases.

3. The fluid sensor according to claim 1, wherein the detection is performed in an area of a boundary between the measuring surface and the body surface.

4. The fluid sensor according to claim 1, wherein the at least one fracture detection element includes at least one fracture detector printed conductor.

5. The fluid sensor according to claim 4, wherein the at least one fracture detector printed conductor extends in at least one area in one of a serpentine and meander pattern in an area of a boundary between the measuring surface and the body surface.

6. The fluid sensor according to claim 4, wherein the at least one fracture detector printed conductor includes at least one first printed conductor segment extending on the measuring surface at least substantially parallel to a boundary between the measuring surface and the body surface and at least one second printed conductor segment extending on the body surface at least substantially parallel to the boundary between the measuring surface and the body surface.

7. The fluid sensor according to claim 4, wherein the at least one fracture detector printed conductor crosses a boundary between the measuring surface and the body surface a plurality of times, in at least one area.

8. The fluid sensor according to claim 7, wherein the conductor crosses the boundary perpendicularly.

9. The fluid sensor according to claim 1, wherein the at least one fracture detection element is situated in at least one area on the measuring surface at a distance of 10 to 100 micrometers from a boundary between the measuring surface and the body surface.

10. The fluid sensor according to claim 9, wherein the distance is 20 to 50 micrometers.

11. The fluid sensor according to claim 9, wherein the distance is 25 micrometers.

12. The fluid sensor according to claim 1, wherein the at least one fracture detection element is situated in at least one area on the body surface at a distance of 10 to 100 micrometers from a boundary between the measuring surface and the body surface.

13. The fluid sensor according to claim 12, wherein the distance is 20 to 50 micrometers.

14. The fluid sensor according to claim 12, wherein the distance is 25 micrometers.

15. The fluid sensor according to claim 1, wherein the fracture detection circuit includes at least one circuit for detecting a resistance.

16. The fluid sensor according to claim 15, wherein the fracture detection circuit further includes at least one threshold circuit for comparing the detected resistance with at least one threshold value and generating at least one control signal as a function of a result of the comparison.

* * * * *